United States Patent
Labhasetwar et al.

(10) Patent No.: US 9,138,416 B2
(45) Date of Patent: *Sep. 22, 2015

(54) SUSTAINED-RELEASE NANOPARTICLE COMPOSITIONS AND METHODS USING THE SAME

(71) Applicant: Board of Regents of the University of Nebraska by and Behalf of the University of Nebraska Medical Center, Omaha, NE (US)

(72) Inventors: Vinod D. Labhasetwar, Cleveland, OH (US); Sanjeeb K. Sahoo, Orissa (IN); Maram K. Reddy, New Delhi (IN)

(73) Assignee: Board of Regents of the University of Nebraska by and behalf of the University of Nebraska Medical Center, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/064,698

(22) Filed: Oct. 28, 2013

(65) Prior Publication Data

US 2014/0050798 A1    Feb. 20, 2014

Related U.S. Application Data

(63) Continuation of application No. 13/690,520, filed on Nov. 30, 2012, now abandoned, which is a continuation of application No. 12/762,580, filed on Apr. 19, 2010, now abandoned, which is a continuation of application No. 11/018,456, filed on Dec. 21, 2004, now Pat. No. 7,727,554.

(51) Int. Cl.
| | |
|---|---|
| *A61K 9/14* | (2006.01) |
| *A61K 9/48* | (2006.01) |
| *A61K 9/00* | (2006.01) |
| *A61K 9/51* | (2006.01) |
| *A61K 31/00* | (2006.01) |
| *A61K 31/436* | (2006.01) |
| *B82Y 5/00* | (2011.01) |

(52) U.S. Cl.
CPC ............. *A61K 9/4816* (2013.01); *A61K 9/0019* (2013.01); *A61K 9/5138* (2013.01); *A61K 9/5146* (2013.01); *A61K 9/5192* (2013.01); *A61K 31/00* (2013.01); *A61K 31/436* (2013.01); *B82Y 5/00* (2013.01); *Y10S 977/773* (2013.01); *Y10S 977/906* (2013.01)

(58) Field of Classification Search
CPC ..... A61K 9/19; A61K 9/5138; A61K 9/5146; A61K 9/5192; A61K 31/00; A61K 31/436; B82Y 5/00; Y10S 977/773; Y10S 977/906
See application file for complete search history.

(56) References Cited

U.S. PATENT DOCUMENTS

| | | |
|---|---|---|
| 6,322,817 B1 | 11/2001 | Maitra et al. |
| 6,759,431 B2 | 7/2004 | Hunter et al. |
| 7,727,554 B2 | 6/2010 | Labhasetwar et al. |
| 2002/0064513 A1 | 5/2002 | Maitra et al. |
| 2003/0054042 A1 | 3/2003 | Liversidge et al. |
| 2003/0059398 A1 | 3/2003 | Ranger et al. |
| 2003/0199425 A1 | 10/2003 | Desai et al. |

FOREIGN PATENT DOCUMENTS

WO    01/87227 A2    11/2001

OTHER PUBLICATIONS

Edelman et al., "Effect of controlled adventitial heparin delivery on smooth muscle cell proliferation following endothelial injury", Proc. Natl. Acad. Sci. SA, 87: 3773-3777 (1990).
Edelman et al., "Perivascular and intravenous administration of basic fibroblast growth factor: Vascular and solid organ deposition", Proc. Natl. Acad. Sci. USA, 90: 1513-1517 (1993).
Edelman et al., "Contrasting Effects of the Intermittent and Continuous Administration of Heparin in Experimental Restenosis", Circulation, 89: 770-776 (1994).
Garcia et al., "Intraoperative Intra-Arterial Urokinase Infusion as an Adjunct to Fogarty Catheter Embolectomy in Acute Arterial Occlusion", Surgery, Gynecology & Obstetrics, 171: 201-205 (1990).
Gupta et al., "Ketorolac entrapped in polymeric micelles: preparation, characterization and ocular anti-inflammatory studies", International Journal of Pharmaceutics, 209: 1-14 (2000).
Labhasetwar et al., "Nanoparticle drug delivery system for restenosis", Advanced Drug Delivery Reviews, 24: 63-85 (1997).
Lanza et al., "Targeted Antiproliferative Drug Delivery to Vascular Smooth Muscle Cells with a Magnetic Resonance Imaging Nanoparticle Contrast Agent", Circulation, 106: 2842-2847 (2002).
Nathan et al., "Tissue engineered perivascular endothelial cell implants regulate vascular injury", Proc. Natl. Acad. Sci. USA, 92: 8130-8134 (1995).

(Continued)

*Primary Examiner* — Satyendra Singh
(74) *Attorney, Agent, or Firm* — Patrick J. Hagan; Dann, Dorfman, Herrell and Skillman, P.C.

(57) ABSTRACT

The present invention is a composition composed of a therapeutic agent encapsulated in a copolymer of an N-alkylacrylamide, a vinyl monomer, and a polyethylene glycol (PEG) conjugate and a method for using the same in the treatment or prevention of a disease or condition.

11 Claims, No Drawings

(56) References Cited

OTHER PUBLICATIONS

Okada et al., "Localized Release of Perivascular Heparin Inhibits Intimal Proliferation after Endothelial Injury without Systemic Anticoagulation", Neurosurgery, 25(6): 892-898 (1989).

Villa et al., "Local Delivery of Dexamethasone for Prevention of Neointimal Proliferation in a Rat Model of Balloon Angioplasty", J. Clin. Invest, 93:p. 1243-1249 (1994).

SUSTAINED-RELEASE NANOPARTICLE COMPOSITIONS AND METHODS USING THE SAME

CROSS-REFERENCE TO RELATED APPLICATIONS

This application is a continuation of U.S. patent application Ser. No. 13/690,520, filed Nov. 30, 2012, which is a continuation of U.S. patent application Ser. No. 12/762,580, filed Apr. 19, 2010 (now abandoned), which is a continuation of U.S. patent application Ser. No. 11/018,456, filed Dec. 21, 2004 (now U.S. Pat. No. 7,727,554, issued Jun. 1, 2010), the entire disclosures of which are incorporated by reference herein.

BACKGROUND OF THE INVENTION

Restenosis is a complex process which is believed to be triggered by blood vessel wall injury following an intervention to relieve an arterial obstruction (e.g., angioplasty, atherectomy, or stenting). Mechanisms contributing to restenosis include elastic recoil, smooth muscle cell migration and proliferation, enhanced extracellular matrix synthesis vessel wall remodeling, and thrombus formation (Haudenschild (1993) *Am. J. Med.* 94:40S-44S; Lovqvist, et al. (1994) *J. Intern. Med.* 233:215-226; Koster, et al. (1995) *Angiology* 46:99-106; Wilcox (1991) *Circulation* 84:432-435; Wilcox (1993) *Am. J. Cardiol.* 72:88E-95E; Wilcox and Blumenthal (1995) *J. Nutr.* 125:631S-638S). Restenosis after an initial successful angioplasty of an atherosclerotic plaque remains the major limitation of coronary angioplasty in humans.

Therapeutic approaches for the prevention of restenosis have focused on either intervening in early events, such as platelet deposition or thrombus formation, or preventing later events, i.e., proliferation of smooth muscle cells and matrix formation. Several classes of therapeutic agents have been used experimentally in animal studies. These have included anticoagulants, anti-inflammatory drugs, anti-platelet agents which can block initial events, and antiproliferative agents which inhibit the later events in the pathogenesis of restenosis (Herrman, et al. (1993). *Drugs* 46:18-52, 249-262; Marmur, et al. (1994) *J. Am. Coll. Cardiol.* 24:1484-1491; Mathias (1991) *Semin. Thromb. Hemostat* 17:14-20). Other approaches to treat restenosis have involved the use of anti-sense oligonucleotides to block transcription of certain cytokines or proto-oncogenes, such as c-myc or c-myb (Wilcox (1993) supra; Bennett, et al. (1994) *J. Clin. Invest.* 93:820-828; Epstein, et al. (1993) *Circulation* 88:1351-1353; Edelman, et al. (1995) *Circ. Res.* 76:176-182) Gene therapy strategies have also been investigated (Wilcox (1993) supra; Muller (1994) *Br. Heart J.* 72:309-312; Nabel, et al. (1990) *Science* 249:1285-1288; Nabel (1995) *Cardiovasc. Res.* 28:445-455; Bennett, et al. (1994) supra; Epstein, et al. (1993) supra; Edelman, et al. (1995) supra; Feldman and Isner (1995) *J. Am. Coll. Cardiol.* 26:826-835).

Modification of the restenosis process by conventional pharmacologic or mechanical approaches (e.g., stenting) (Wilensky, et al. (1993) *Trends Cardiovasc. Med.* 3:163-170) have been used in the clinical setting. Drug therapies have included antiplatelet and anticoagulant agents, calcium channel antagonists, inhibitors of angiotensin converting enzyme, corticosteroids, and fish oil diet (Herrman, et al. (1993) supra). Mechanical approaches include deployment of metallic or polymeric stents in the artery to inhibit elastic recoiling which usually occurs within hours following angioplastic procedure and results in renarrowing of the artery lumen (Herrman, et al. (1993) supra; De Scheerder, et al. (1995) *Atherosclerosis* 114:105-114; De Foley, et al. (1993) *Am. Heart J.* 125:686-694; Kuntz, et al. (1993) *J. Am. Coll. Cardiol.* 21:15-25; Lambert, et al. (1994) *Circulation* 90:1003-1011; Mitchel and McKay (1995) *Cathet. Cardiovasc. Diagn.* 34:149-154; Buchwald, et al. (1993) *J. Am. Coll. Cardiol.* 21:249-254). Other approaches include atherectomy, local treatment of arterial lesions with laser, thermal energy, and β- and γ-radiations following interventional procedures (Buchwald, et al. (1992) *Am. Heart J.* 123:878-885; Kouek, et al. (1992) *Circulation* 86:1249-1256; Israel, et al. (1991) *J. Am. Coll. Cardiol.* 18:1118-1119).

Administration of therapeutic agents at the site of arterial injury rather than by systemic administration has been discussed (Labhasetwar, et al. (1997) *Adv. Drug Del. Rev.* 24:63-85). Experimental studies in animal models of restenosis have been used to investigate local delivery of therapeutics for the prevention of restenosis (Lambert, et al. (1994) supra; Garcia, et al. (1990) *Surg. Gynecol. Obstet.* 171:201-205; Edelman, et al. (1990) *Proc. Nat. Acad. Sci. USA* 87:3773-3777; Edelman, et al. (1993) *Proc. Nat. Acad. Sci. USA* 90:1513-1517; Edelman and Karnovsky (1994) *Circulation* 89:770-776; Nathan, et al. (1995) *Proc. Nat. Acad. Sci. USA* 92:8130-8134; Okada, et al. (1989) *Neurosurgery* 25:892-898; Villa, et al. (1994) *J. Clin. Invest.* 93:1243-1249; Villa, et al. (1995) *Circ. Res.* 76:505-513). Adventitial drug implants (Edelman, et al. (1990) supra; Villa, et al. (1994) supra; Simons, et al. (1992) *Nature* 359:67-70; Simons, et al. (1994) *J. Clin. Invest.* 93:2351-2356), stents (Lincoff, et al. (1994) *J. Am. Coll. Cardiol.* 23:18A; Jeong, et al. (1994) *Circulation* 92:I37), and catheter-based delivery systems (Steg, et al. (1994) *Circulation* 90:1648-1656; Fernandez, et al. (1994) *Circulation* 89:1518-1522) have been disclosed. Further, Lanza, et al. ((2002) *Circulation* 106:2842) teach targeted paramagnetic nanoparticles containing paclitaxel for the prevention of restenosis after angioplasty.

U.S. patent application Ser. No. 09/847,945 teaches methods for treating hyperplasia in a subject by delivering at least one drug in nanoparticle form and dispersed in a biocompatible protein. This reference discloses the use of paclitaxel, rapamycin, steroids, and the like, as suitable candidates to inhibit proliferation and migration of cells. This reference does not teach block co-polymer nanoparticles.

U.S. Pat. No. 6,322,817 teaches a pharmaceutical formulation of paclitaxel, wherein the paclitaxel is entrapped into nanoparticles comprising at least one type of amphiphilic monomer which is polymerized by adding an aqueous solution of cross-linking agent. This reference discloses a preferred combination of amphiphilic monomers comprising vinyl pyrrolidone, N-isopropylacrylamide, and monoester of polyethylene glycol maleic anhydride cross-linked with a bi-functional vinyl derivative such as N,N'-methylene bis-acrylamide useful in the treatment of pathological conditions arising out of excessive proliferation of cells such as rheumatoid arthritis or cancer.

U.S. Pat. No. 6,759,431 discloses methods for treating or preventing diseases associated with body passageways by delivering to an external portion of the body passageway a therapeutic agent such as paclitaxel, or an analogue or derivative thereof encapsulated in polymeric carriers.

Intravenous or oral delivery of agents for preventing disease or conditions is generally ineffective because these routes of delivery do not provide a therapeutic dose of the agent to the target site for a prolonged period of time. Therefore, there is a need in the art for site-specific therapeutics to prevent the localized pathophysiologic process of select disease or conditions. The present invention meets this long-felt need.

SUMMARY OF THE INVENTION

The present invention is a sustained-release nanoparticle composition composed of a copolymer of an N-alkylacrylamide, a vinyl monomer, and a polyethylene glycol conjugate. In one embodiment, the N-alkylacrylamide, vinyl monomer, and polyethylene glycol conjugate are in a weight per weight ratio of 70-90:9-20:1-10. In another embodiment, the N-alkylacryalmide comprises N-methyl-N-n-propylacrylamide, N-methyl-N-isopropylacrylamide, N-propylmethacrylamide, N-isopropylacrylamide, N-n-diethylacrylamide, N-isopropylmethacrylamide, N-cyclopropylacrylamide, N-ethylmethyacrylamide, N-methyl-N-ethylacrylamide, N-cyclopropylmethacrylamide, or N-etjylacrylamide. In a further embodiment, the vinyl monomer comprises a vinyl alcohol, a vinyl ether, a vinyl ester, a vinyl halide, a vinyl acetate, or a vinyl pyrrolidone. In yet a further embodiment, the polyethylene glycol conjugate comprises PEGylated maleic acid, PEGylated vinylsulfone, PEGylated iodoacetamide or PEGylated orthopyridyl disulfide. In particular embodiments, the sustained-release nanoparticle composition further contains a therapeutic agent such as an antibiotic, anti-restenotic agent, anti-proliferative agent, anti-neoplastic, chemotherapeutic agent, cardiovascular agent, anti-inflammatory agent, immunosuppressive agent, or anti-tissue damage agent. Such nanoparticle compositions generally have a diameter in the range of 20 nm to 100 nm and are used locally for the prevention or treatment of diseases or conditions.

The present invention is also a method for using a sustained-release nanoparticle composition for preventing or treating a disease or condition. The method involves locally administering an effective amount of a sustained-release nanoparticle composition containing a therapeutic agent to a patient having or at risk of having a disease or condition thereby preventing or treating the disease or condition in the patient. In particular embodiments, the patient is at risk of restenosis, i.e., the patient has undergone angioplasty, atherectomy, or stenting.

DETAILED DESCRIPTION OF THE INVENTION

It has now been appreciated that a therapeutic agent encapsulated in a nanoparticle composed of a copolymer of an N-alkylacrylamide, a vinyl monomer, and a polyethylene glycol (PEG) conjugate can be administered locally to effectively deliver high concentrations of the therapeutic agent. In particular, improved loading efficiency of the therapeutic agent into nanoparticles has been achieved with higher molar ratios of the N-alkylacrylamide component of the nanoparticle. Therapeutic agents entrapped in the nanoparticles disclosed herein are released slowly as the nanoparticles dissociate, thus providing sustained drug release characteristics. A nanoparticle of the present invention serves as an effective drug carrier for intraluminal drug delivery because of its nanometer size range that results in better drug uptake and penetration in the arterial wall than that of a larger drug carrier system such as a microparticle or liposome.

By way of illustration, a specific therapeutic agent-nanoparticle composition was prepared to demonstrate sustained-release, biocompatibility, arterial localization, inhibition of cell proliferation, and prevention of hyperplasia in a rat carotid artery model of restenosis. The illustrative composition consisted of rapamycin, a potent macrolide antibiotic which is known to inhibit proliferation and migration of vascular smooth muscle cells (VSMCs), and polymeric nanoparticles synthesized using a copolymer of N-isopropylacrylamide (NIPAM), vinyl pyrrolidone (VP), and PEGylated maleic acid (PEGMA) (80:15:5) which were cross-linked with N,N'-methylene bis-acrylamide (MBA). When compared to nanoparticles lacking PEG, the addition of PEG to the nanoparticle composition was found to provide greater stability to the nanoparticles, decreased aggregation and increased drug loading. On a weight per weight basis, nanoparticles lacking a PEG conjugate (i.e., containing NIPAM: VP, 80:20) incorporated 2.5% of rapamycin. In contrast, preformed nanoparticles containing a PEG conjugate (i.e., NIPAM:VP:PEGMA, 80:15:5) incorporated up to 4.5% of rapamycin.

Rapamycin-loaded nanoparticles exhibited sustained-release of the loaded drug under in vitro conditions. The release rate was high during the initial phase and decreased exponentially with time (Table 1).

TABLE 1

| Days | Cumulative % Release of Rapamycin (±SEM) |
|---|---|
| 0.5 | 3.81 (±0.18) |
| 1 | 20.05 (±0.45) |
| 2 | 33.81 (±1.67) |
| 4 | 49.39 (±1.43) |
| 6 | 60.32 (±2.28) |
| 10 | 67.26 (±1.20) |
| 14 | 73.77 (±1.78) |
| 21 | 79.35 (±1.94) |
| 28 | 84.36 (±2.15) |

To demonstrate biocompatibility, vascular smooth muscle cells were exposed for 48 hours to various concentrations of nanoparticles lacking rapamycin (0, 10, 50, 100, and 1000 µg/mL) and cell viability was determined using a standard MTS assay. The nanoparticles exhibited no toxic effect to vascular smooth muscle cells in vitro up to a dose of 1000 µg/mL.

To demonstrate the anti-proliferative effects of rapamycin-loaded nanoparticles on vascular smooth muscle cells, cells were incubated with various concentrations (1, 10, 100, 1000 ng/mL) of rapamycin either in solution (i.e., dissolved in methanol and diluted in cell culture medium) or loaded in, nanoparticles. Proliferation was measured using an MTS assay. Although rapamycin in solution and rapamycin-loaded nanoparticles exhibited a similar dose-dependent inhibition of vascular smooth muscle cell proliferation, inhibition with rapamycin-loaded nanoparticles was significantly greater at later time points. For example, rapamycin (1 ng/mL) in solution and in nanoparticles showed similar inhibition at 5 days; however, at 8 days, rapamycin in nanoparticles demonstrated 20% more inhibition than rapamycin in solution (Table 2). Therefore, rapamycin-loaded nanoparticles demonstrate sustained inhibition of vascular smooth muscle cell proliferation.

TABLE 2

| Treatment | Cell Viability (Absorbance ± SEM) | | |
|---|---|---|---|
| | Day 2 | Day 5 | Day 8 |
| Medium | 0.332 ± 0.010 | 0.748 ± 0.048 | 1.065 ± 0.068 |
| | 0.357 ± 0.047 | 0.758 ± 0.049 | 1.075 ± 0.061 |
| | 0.343 ± 0.029 | 0.758 ± 0.049 | 1.087 ± 0.077 |
| | 0.344 ± 0.026 | 0.773 ± 0.035 | 1.059 ± 0.049 |
| Control | 0.316 ± 0.027 | 0.712 ± 0.054 | 1.016 ± .031 |

TABLE 2-continued

| Treatment | Cell Viability (Absorbance ± SEM) | | |
|---|---|---|---|
| | Day 2 | Day 5 | Day 8 |
| Nanoparticle | 0.346 ± 0.019 | 0.705 ± 0.039 | 1.050 ± 0.021 |
| | 0.354 ± 0.015 | 0.707 ± 0.039 | 1.050 ± 0.021 |
| | 0.419 ± 0.028 | 0.699 ± 0.031 | 1.017 ± 0.025 |
| Rapamycin in Solution | | | |
| 1 ng/mL | 0.177 ± 0.017 | 0.363 ± 0.019 | 0.633 ± 0.019 |
| 10 ng/mL | 0.199 ± 0.023 | 0.369 ± 0.036 | 0.688 ± 0.040 |
| 100 ng/mL | 0.195 ± 0.014 | 0.325 ± 0.023 | 0.692 ± 0.040 |
| 1000 ng/mL | 0.196 ± 0.011 | 0.354 ± 0.015 | 0.693 ± 0.058 |
| Rapamycin-loaded Nanoparticle | | | |
| 1 ng/mL | 0.184 ± 0.012 | 0.364 ± 0.027 | 0.489 ± 0.044 |
| 10 ng/mL | 0.196 ± 0.027 | 0.368 ± 0.029 | 0.431 ± 0.037 |
| 100 ng/mL | 0.178 ± 0.011 | 0.326 ± 0.019 | 0.402 ± 0.020 |
| 1000 ng/mL | 0.196 ± 0.007 | 0.362 ± 0.069 | 0.485 ± 0.027 |

The effect of rapamycin-loaded nanoparticles on the cell cycle was determined by flow cytometry analysis of DNA in vascular smooth muscle cells. Flow cytometry data demonstrated that the anti-proliferative effect of rapamycin was primarily due to inhibition of cell-cycle progression at G1 checkpoint; the percentage of cells in G0-G1 phase was 74.6% for the rapamycin-loaded nanoparticle-treated cells compared to 62.7% in the untreated group. Similarly, there was a lower percentage of cells in the proliferative S phase in the treatment group as compared to that in the control (13.5% vs. 24.25%). (Table 3).

TABLE 3

| Treatment | $G_0/G_1$ | S | $G_2/M$ | % Apoptosis |
|---|---|---|---|---|
| Medium | 65.70 | 21.25 | 13.05 | 0.07 |
| Control Nanoparticle | 67.96 | 19.35 | 12.67 | 0.12 |
| Rapamycin-Loaded Nanoparticle | 74.56 | 13.53 | 11.91 | 0.06 |
| Rapamycin in Solution | 73.48 | 15.41 | 11.12 | 0.06 |

The efficacy of rapamycin-loaded nanoparticles was demonstrated in a rat carotid artery model of restenosis. Morphometric analysis of arterial sections demonstrated significantly reduced intima to media (I/M) ratio with localized delivery of rapamycin-loaded nanoparticles compared to control nanoparticles (I/M=1.60±0.03 vs. 3.15±0.10; P<0.006)(Table 4). Intraperitoneal administration of the same dose of rapamycin-loaded nanoparticles demonstrated a marginal effect on inhibition of restenosis as compared to control (I/M=2.8±0.11 vs. 3.15±0.10; P<0.006), indicating that the inhibitory effect was primarily due to localized delivery of rapamycin. Inhibition of hyperplasia resulted in increased lumen diameter in locally delivered rapamycin-loaded micellar nanosystem as compared to other controls (local rapamycin-loaded nanoparticle group, 0.29±0.002 mm$^2$; intraperitoneal rapamycin-loaded nanoparticles group, 0.14±0.009 mm$^2$; local non-drug void nanoparticles group, 0.17±0.003 mm$^2$; P<0.006).

TABLE 4

| Treatment | Intima/ Media Ratio (mean ± SEM) | Cross-Sectional Area of Lumen (mm$^2$ ± SEM) |
|---|---|---|
| Uninjured Artery | — | 0.368 ± 0.012 |
| Control Nanoparticles | 3.15 ± 0.10 | 0.17 ± 0.002 |
| Rapamycin-Loaded Nanoparticles (I.P.) | 2.87 ± 0.11 | 0.14 ± 0.009 |
| Rapamycin-Loaded Nanoparticles (Local) | 1.60 ± 0.03 | 0.29 ± 0.002 |

Immunohistochemical staining with anti-SM antibody against α-actin (α-SMA) showed greater expression of SMA positive cells in the neointima and adventitia of the arteries of the control group as compared to that in the rapamycin-treated group. Immunohistochemical staining with anti-PCNA antibody showed a significantly greater number of PCNA positive cells in the neointima and adventitia in control than in the treatment group. These results indicated that rapamycin delivery suppressed the proliferation of VSMCs. The arterials sections in the treatment group demonstrated significantly greater re-endothelization of the injured artery as compared to control (82% vs. 28%).

Further, nanoparticle localization studies were conducted using 6-coumarin fluorescent dye-loaded nanoparticles and rapamycin-loaded nanoparticles. Of the two carotid arteries, only one artery was injured and infused with nanoparticles. Rapamycin- and dye-loaded nanoparticles were found to localize in the arterial wall of the artery infused with nanoparticles, not the contra-lateral artery. Confocal microscopy analysis of the arterial sections demonstrated localization of nanoparticles in all the layers (intima, media and adventitia) at 1 hour; however, at 24 hours the overall fluorescence activity was reduced but was greater in the tunica media than in the intimal layer of the arterial wall. When quantified, 1.5±0.06 μg of rapamycin was present per milligram of artery at one hour after administration (Table 5). No rapamycin was detected in the non-injured contra-lateral carotid artery. Therefore, based upon the amount of rapamycin present in a 10-15 mm segment of artery (3.2 to 4 mg of tissue), and the amount of drug administered, the efficiency of rapamycin uptake in the target artery was 9.1% when delivered locally via nanoparticles.

TABLE 5

| Time after Administration | Rapamycin (μg/mg tissue) (±SEM) |
|---|---|
| 1 hour | 1.5 (±0.06) |
| 1 day | 0.12 (±0.01) |
| 3 days | 0.06 (±0.03) |
| 7 days | 0.05 (±0.01) |

Having appreciated the utility of a therapeutic agent encapsulated in a nanoparticle composed of an N-alkylacrylamide, a vinyl monomer, and a PEG conjugate for local delivery and prevention of a condition such as restenosis, the present invention is a sustained-release (i.e., more than 2 to 3 weeks) nanoparticle composition and a method for using the same for the prevention or treatment of a disease or condition.

Given the improved loading efficiency associated with higher molar ratios of the N-alkylacrylamide component of the nanoparticle, one embodiment of the present invention encompasses molar ratios of the N-alkylacrylamide, vinyl monomer, and polyethylene glycol conjugate in the range of 70-90:9-20:1-10, respectively. In another embodiment, the molar ratios of N-alkylacrylamide, vinyl monomer, and polyethylene glycol conjugate are in the range of 75-85:12-18:2-8, respectively. In a particular embodiment, the molar ratio of the N-alkylacrylamide, vinyl monomer, and polyethylene glycol conjugate are desirably 80:15:5, respectively.

As used herein, an N-alkylacrylamide is a hydrophobic monomer having an alkyl group of $C_3$ to $C_6$. By way of example, an N-alkylacrylamide can be N-methyl-N-n-propylacrylamide, N-methyl-N-isopropylacrylamide, N-propylmethacrylamide, N-isopropylacrylamide, N,n-diethylacrylamide, N-isopropylmethacrylamide, N-cyclopropylacrylamide, N-ethylmethyacrylamide, N-methyl-N-ethylacrylamide, N-cyclopropylmethacrylamide, N-ethylacrylamide, or the like.

A vinyl monomer used in the context of the present invention is a hydrophilic monomer having a relatively high molecular weight (e.g., in the range of approximately 100,000 to 2,000,000, more typically in the range of approximately 500,000 to 1,500,000). Suitable vinyl monomers include, but are not limited to vinyl alcohol, vinyl ether, vinyl ester, vinyl halide, vinyl acetate; vinyl pyrrolidone, or copolymers thereof.

Polyethylene glycol conjugates and methods for preparing the same are well-known in the art (Roberts, et al. (2002) *Adv. Drug Deliv. Rev.* 54:459-476) and it is contemplated that any suitable conjugate can be used in the nanoparticles of the instant invention. In general, the PEG moiety of the PEG conjugate is a linear compound having a molecular weight in the range of 2,000 to 50,000. It is contemplated that any PEG moiety can be used; however, the molecular weight of the PEG moiety directly influences the size of the resulting nanoparticle (i.e., the higher the molecular weight, the larger the diameter of the nanoparticle). For example, it was found that the addition of a PEG conjugate, having a PEG moiety with a molecular weight of 5000, to a nanoparticle composed of NIPAM and VP increased the diameter of the resulting nanoparticle by 5-10 nm when compared to the diameter of a NIPAM/VP nanoparticle lacking a PEG conjugate. Accordingly, in one embodiment, the PEG moiety of the PEG conjugate has a molecular weight in the range of 3,000 to 10,000. In another embodiment, the PEG moiety of the PEG conjugate has a molecular weight in the range of 4,000 to 7,000. In a particular embodiment, the PEG moiety of the PEG conjugate has a molecular weight of 5,000. Particularly suitable PEG conjugates include, by way of example, PEGylated maleic acid, vinylsulfone, iodoacetamide or orthopyridyl disulfide.

While the selected cross-linking agent used is not crucial, suitable cross-linking agents for use in producing the nanoparticles of the present invention include, but are not limited to, N,N'-methylene bis-acrylamide or N,N'-cystamine bis-acrylamide.

The biodegradable nanoparticles of the present invention can be prepared by mixing the monomers indicated herein in the presence of a cross-linking agent and polymerizing the mixture by free radical polymerization reaction using an initiator (e.g., ammonium persulfate, benzoyl perozide, or AIBN (2,2'-azo bisisobutyronitrile)). The hydrophobic moieties of the resulting polymeric chains remain buried inside the nanoparticles which help dissolution of drug and the hydrophilic moieties are extended outside the surface of the nanoparticles. These biodegradable nanoparticles have an average diameter of 20 nm to 100 nm and are particularly suitable for local delivery of therapeutic agents.

A therapeutic agent as used herein refers to an agent which can mitigate, cure, treat or prevent a disease or condition. It is particularly desirable that the therapeutic agent be capable of exerting it effect locally (i.e., at or near the site of the disease or condition). Exemplary therapeutic agents include, but are not limited to, antibiotics, antirestenotics, anti-proliferative agents, anti-neoplastic agents, chemotherapeutic agents, cardiovascular agents, anti-inflammatory agents, immunosuppressive agents, anti-apoptotic and anti-tissue damage agents.

In the context of the present invention, an antibiotic is intended to include antibacterial, antimicrobial, antiviral, antiprotozoal and antifungal agents. Representative examples of such agents include antibiotics such as aminoglycosides (e.g., streptomycin, gentamicin, tobramycin); 1st, 2nd, and 3rd generation cephalosporins (e.g., cephalothin, cefaclor, cefotaxime, moxalactam, other semisynthetic cephalosporins such as cefixime); penicillins (e.g., penicillin G, ampicillin, amoxicillin); quinolones (e.g., ciprofloxacin, nalidixic acid, ofloxacin, tosufloxacin, lomefloxacin); sulfonamides (e.g., sulfamethizole, sufisoxazole, sulfasalazine, trimethoprim); tetracyclines (e.g., doxycycline, methacycline); macrolides (e.g., erythromycins); monobactams (e.g., aztreonam, loracarbef); and miscellaneous agents such as novobiocin, rifampin, bleomycin, chloramphenicol, clindamycin, kanamycin, neomycin, spectinomycin, amphotericin B, colistin, nystatin, polymyxin B, cycloserine, methenamine, metronidazole, rifabutan, spectinomycin, trimethoprim, bacitracin, vancomycin, other β-lactam antibiotics. Antifungal agents include flucytosine, fluconazole, griseofluvin, ketoconazole and miconazole. Antiviral and AIDS agents include acyclovir, amantadine, didanosine (formerly ddI), griseofulvin, flucytosine, foscamet, ganciclovir, idoxuridine, miconazole, clotrimazole, pyrimethamine, ribavirin, rimantadine, stavudine (formerly d4T), trifluridine, trisulfapyrimidine, valacyclovir, vidarabine, zalcitabine (formerly ddC) and zidovudine (formerly AZT). Representative examples of antiprotozoal agents include pentamidine isethionate, quinine, chloroquine, and mefloquine.

Representative examples of restenosis therapeutic agents include, for example, anti-angiogenic agents such as anti-invasive factor (Eisentein, et al. (1975) *Am. J. Pathol.* 81:337-346; Langer, et al. (1976) *Science* 193:70-72; Horton, et al. (1978) *Science* 199:1342-1345), retinoic acid and derivatives thereof which alter the metabolism of extracellular matrix components to inhibit angiogenesis, tissue inhibitor of metalloproteinase-1, tissue inhibitor of metalloproteinase-2, plasminogen activator inhibitor-1, plasminogen activator inhibitor-2, and anginex (Griffioen, et al. (2001) *Biochem. J.* 354(Pt 2):233-42); collagen inhibitors such as halofuginone or batimistat; antisense oligonucleotides directed to nucleic acid sequences encoding c-myc or c-myb; growth factor inhibitors such as tranilast, trapidil or angiopeptin; antioxidants such as probucol, anti-thrombotics such as heparin or abciximab, anti-proliferative agents such as AG-1295 (Fishbein, et al. (2000) *Arterioscler. Thromb. Vasc. Biol.* 20:667), tyrphostin (Banai, et al. (2005) *Biomaterials* 26(4):451-61), pacitaxel or other taxanes (Scheller, et al. (2004) *Circulation* 110(7):810-4), isoflavones (Kanellakis, et al. (2004) *Atherosclerosis* 176(1):63-72), rapamycin or derivatives or analogs thereof (Schachner, et al. (2004) *Ann. Thorac. Surg.* 77(5): 1580-5), vincristine, vinblastine, HMG-CoA reductase inhibitors, doxorubicin, colchicines, actinomycin D, mitomycin C, cyclosporine, or mycophenolic acid; anti-inflammatory agents such as dexamethasone (Liu, et al. (2004) *Expert Rev. Cardiovasc. Ther.* 2(5):653-60), methylprednisolone, or gamma interferon; and the like which exhibits antirestenotic activity.

Other therapeutic agents that can be utilized in accordance with the present invention include anti-proliferative, anti-neoplastic or chemotherapeutic agents to prevent or treat tumors. Representative examples of such agents include androgen inhibitors; antiestrogens and hormones (e.g., flutamide, leuprolide, tamoxifen, estradiol, estramustine, megestrol, diethylstilbestrol, testolactone, goserelin, medroxyprogesterone); cytotoxic agents (e.g., altretamine, bleomycin, busulfan, carboplatin, carmustine(BiCNU), cisplantin, cladribine, dacarbazine, dactinomycin, daunorubicin, doxorubicin, estramustine, etoposide, lomustine, cyclophosphamide, cytarabine, hydroxyurea, idarubicin, interferon alpha-2a and -2b, ifosfamide, mitoxantrone, mitomycin, paclitaxel, streptozocin, teniposide, thiotepa, vinblastine, vincristine, vinorelbine); antimetabolites and antimitotic agents (e.g., floxuridine, 5-fluorouracil, fluarabine, interferon alpha-2a and -2b, leucovorin, mercaptopurine, methotrexate, mitotane, plicamycin, thioguanine, colchicines); folate antagonists and other anti-metabolites; vinca alkaloids; nitrosoureas; DNA alkylating agents; purine antagonists and analogs; pyrimidine antagonists and analogs; alkyl solfonates; enzymes (e.g., asparaginase, pegaspargase); and toxins (e.g., ricin, abrin, diphtheria toxin, cholera toxin, gelonin, pokeweed antiviral protein, tritin, *Shigella* toxin, and *Pseudomonas* exotoxin A).

Further therapeutic agents that can be utilized within the present invention include cardiovascular agents such as anti-hypertensive agents; adrenergic blockers and stimulators (e.g., doxazosin, guanadrel, guanethidine, pheoxybenzamine, terazosin, clonidine, guanabenz); alpha-/beta-adrenergic blockers (e.g., labetalol); angiotensin converting enzyme (ACE) inhibitors (e.g., benazepril, catopril, lisinopril, ramipril); ACE-receptor antagonists (e.g., losartan); beta blockers (e.g., acebutolol, atenolol, carteolol, pindolol, propranolol, penbatolol, nadolol); calcium channel blockers (e.g., amiloride, bepridil, nifedipine, verapamil, nimodipine); antiarrythmics, groups I-IV (e.g., bretylium, lidocaine, mexiletine, quinidine, propranolol, verapamil, diltiazem, trichlormethiazide, metoprolol tartrate, carteolol hydrochloride); and miscellaneous antiarrythmics and cardiotonics (e.g., adenosine, digoxin, caffeine, dopamine hydrochloride, digitalis).

Other therapeutic agents that can be used in accord with the present invention include anti-inflammatory agents. Representative examples of such agents include nonsteroidal agents (NSAIDS) such as salicylates, diclofenac, diflunisal, flurbiprofen, ibuprofen, indomethacin, mefenamic acid, nabumetone, naproxen, piroxicam, ketoprofen, ketorolac, sulindac, tolmetin. Other anti-inflammatory drugs include steroidal agents such as beclomethasone, betamethasone, cortisone, dexamethasone, fluocinolone, flunisolide, hydorcortisone, prednisolone, and prednisone. Immunosuppressive agents are also contemplated (e.g., adenocorticosteroids, cyclosporin).

Other therapeutic agents include anti-tissue damage agents. Representative examples of such agents include superoxide dismutase; immune modulators (e.g., lymphokines, monokines, interferon α and β); and growth regulators (e.g., IL-2, tumor necrosis factor, epithelial growth factor, somatrem, fibronectin, GM-CSF, CSF, platelet-derived growth factor, somatotropin, rG-CSF, epidermal growth factor, IGF-1).

In a particular embodiment, the therapeutic agent is an anti-restenotic agent such as rapamycin (i.e., sirolimus) or a derivative or analog thereof, e.g., everolimus or tacrolimus (Grube, et al. (2004) *Circulation* 109(18):2168-71; Grube and Buellesfeld (2004) *Herz* 29(2):162-6).

In another embodiment, the therapeutic agent is an anti-apoptotic agent such as Galectin-3; (-)deprenyl; monoamine oxidase inhibitors (MAO-I) such as selegiline and rasagiline; Rapamycin; or quercetin.

In general, the therapeutic agent can be added concurrent with or subsequent to the preparation of the nanoparticles. The therapeutic agent is desirably loaded into preformed nanoparticles with loading of at least 3% w/w of agent to nanoparticles. Generally, it is desirable to achieve loading of up to 10% w/w of therapeutic agent to nanparticle.

The present invention further relates to a method for preventing or treating a disease or condition using the nanoparticles disclosed herein. The method involves locally administering an effective amount of a composition containing a therapeutic agent encapsulated in a nanoparticle composed of an N-alkylacrylamide, a vinyl monomer, and a PEG conjugate to a patient having or at risk of a disease or condition thereby preventing or treating the disease or condition in the patient.

A patient having a disease or condition, in general, exhibits one or more signs associated with the disease or condition. A patient at risk of a disease or condition is intended to include a patient that has a familial history of the disease or condition or due to other circumstances may be predisposed to develop the disease or condition. For example, a patient at risk of developing restenosis would include a patient that has undergone intervention to relieve an arterial obstruction (e.g., angioplasty, atherectomy, or stenting) and may be at risk of developing stenosis. When delivered locally (e.g., at the site of injury or at the site of a tumor), a composition of the present invention can deliver a sustained-release of the therapeutic agent to prevent or treat a select disease or condition. In general, an effective amount is considered an amount that causes a measurable change in one or more signs or symptoms associated with the select disease or condition when compared to otherwise same conditions wherein the agent is not present. For example, an effective amount of an anti-proliferative agent would cause a measurable decrease in hyperplasia or cell proliferation as compared to cells not exposed to the anti-proliferative agent. Further, an effective amount of an antibiotic would result in an inhibition or decrease in the number of viable bacterial, fungal, or protozoan cells.

Nanoparticle compositions of the present invention can be administered either alone, or in combination with a pharmaceutically or physiologically acceptable carrier, excipient or diluent. Generally, such carriers should be nontoxic to recipients at the dosages and concentrations employed. Ordinarily, the preparation of such compOsitions entails combining the nanoparticle composition of the present invention with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients.

As demonstrated herein, local drug delivery facilitates high regional concentrations of the therapeutic agent with prolonged retention at lower doses with reduced systemic toxicity. In addition, therapeutic agents with a relatively short half-life, such as recombinant proteins and peptides, and other biologically unstable biomolecules such as nucleic acids and oligonucleotides, can also be delivered locally with minimal loss in therapeutic activity before uptake by the target cells or tissue. Furthermore, the hydrophobic core of the nanoparticle composition of the present invention will find use in the encapsulation and delivery of highly hydrophobic therapeutic agents. Moreover, local drug delivery reduces patient-to-patient variability in drug pharmacokinetics, which is usually associated with intravenous or oral routes of drug administration.

Nanoparticle compositions provided herein can be prepared for local administration by a variety of different routes, including for example, directly to site of the disease or condition (e.g., a site of injury or tumor) under direct vision (e.g., at the time of surgery or via endoscopic procedures) or via percutaneous drug delivery to the exterior (adventitial) surface of the site of the disease or condition (e.g., perivascular delivery). As an alternative, the placement of pellets via a catheter or trocar can also be accomplished.

Perivascular drug delivery involves percutaneous administration of the nanoparticle composition using a needle or catheter directed via ultrasound, computed tomography, fluoroscopic, positron emission tomography, magnetic resonance imaging or endoscopic guidance to the site of the disease or condition. Alternatively, the procedure can be performed intra-operatively under direct vision or with additional imaging guidance. In the case of restenosis or other cardiovascular diseases, such a procedure can also be performed in conjunction with endovascular procedures such as angioplasty, atherectomy, or stenting or in association with an operative arterial procedure such as endarterectomy, vessel or graft repair or graft insertion.

For example, in a patient with narrowing of the superficial femoral artery, balloon angioplasty would be performed in the usual manner (i.e., passing a balloon angioplasty catheter down the artery over a guide wire and inflating the balloon across the lesion). Prior to, at the time of, or after angioplasty, a needle would be inserted through the skin under ultrasound, fluoroscopic, or CT guidance and a therapeutic agent (e.g., rapamycin encapsulated into a sustained-release nanoparticle) would be infiltrated through the needle or catheter in a circumferential manner directly around the area of narrowing in the artery. This could be performed around any artery, vein or graft, but ideal candidates for this intervention include diseases of the carotid, coronary, iliac, common femoral, superficial femoral and popliteal arteries and at the site of graft anastomosis. Logical venous sites include infiltration around veins in which indwelling catheters are inserted.

Those of ordinary skill in the art can readily identify the appropriate therapeutic agent for the prevention or treatment of a select disease or condition and optimize effective doses and co-administration regimens as determined by good medical practice and the clinical condition of the individual patient. Regardless of the manner of administration, it can be appreciated that the actual preferred amounts of active agent in a specific case will vary according to the particular formulation and the manner of administration. The specific dose for a particular patient depends on age, body weight, general state of health, on diet, on the timing and route of administration, and on medicaments used in combination and the severity of the particular disorder to which the therapy is applied. Dosages for a given subject can be determined using conventional considerations, e.g., by customary comparison of the differential activities of the selected agent and of a known agent, such as by means of an appropriate conventional pharmacological protocol.

The invention is described in greater detail by the following non-limiting examples.

Example 1

Formulation of Rapamycin-Loaded Nanoparticles

N-Isopropylacrylamide (NIPAM) was purchased from Sigma Chemical Co (St. Louis, Mo.) and purified by recrystallization from n-hexane before polymerization. N-Vinyl pyrrolidone (VP) was obtained from Fluka Chemie AG and RdH (Laborchemikalien GmbH & Co. KG) and was distilled before use. N,N'-Methylene bis-acrylamide (MBA), ferrous ammonium sulfate (FAS), ammonium persulphate (APS), TWEEN®-80, and rapamycin were purchased from Sigma (St. Louis, Mo.). All salts used in the preparation of buffers were from Fisher Scientific (Pittsburgh, Pa.). All aqueous solutions were prepared with distilled and deionized water (Water pro plus, Labconco, Kansas City, Mo.).

Nanoparticles were formulated through random, free radical polymerization. In brief, water-soluble monomers NIPAM, VP and PEGylated maleic ester were used in a various molar ratios and then cross-linked with MBA. FAS was used to activate the polymerization reaction. In a typical optimized protocol, 19 μL of freshly distilled VP, 80 mg of NIPAM, and 10 mg of PEGylated maleic ester were dissolved in 10 mL water. To this aqueous solution was added 28 μL of MBA (49 mg/mL) and nitrogen gas was passed through the solution for 30 minutes to remove dissolved oxygen. Subsequently, 50 μL of 10% FAS and 50 μL of saturated APS solution were added to initiate the polymerization reaction. The polymerization reaction was carried out at 30° C. under nitrogen atmosphere for 24 hours. The nanoparticle dispersion thus formed was dialyzed overnight against distilled water (2 L) using a SPECTROPORE® dialysis bag (molecular weight cutoff 12-kD, SPECTRUM®, Laguna Hills, Calif.,) for 24 hours with water changed twice to remove unreacted monomers and electrolytes. The aqueous dispersion of nanoparticles was lyophilized (−80° C., <10 μm mercury pressure, SENTRY™, Virtis, Gardiner, N.Y.) for 48 hours to obtain a dry power, which was subsequently used for drug loading.

For rapamycin loading, 20 mg of the lyophilized nanoparticles was dispersed in 2 mL of distilled water by vortexing for 2 minutes. To this dispersion was added 250 μL of methanolic solution of rapamycin (4 mg/mL) with constant stirring on a magnetic stir plate for 2 hours. This allowed rapamycin to partition into the hydrophobic core of the nanoparticles. The free rapamycin was separated by overnight dialysis of the dispersion against 1 L of distilled water using a SPECTROPORE® dialysis bag (molecular weight cutoff size 12-kD). The drug-loaded nanoparticles were then lyophilized for 48 hours as described herein. For arterial localization of nanoparticles, the formulation contained a fluorescent dye, 6-coumarin. The dye solution (100 μL, 0.5 mg/mL) was added into the micellar dispersion instead of a drug solution. Localization of the dye, and hence the nanoparticles was carried out confocal microscopy.

The resulting nanoparticles were characterized by an $^1$H NMR spectra of monomers and polymers recorded on Varian 500 MHz spectrophotometer. Nanoparticles were dissolved in $D_2O$ to demonstrate that the polymerization was complete. Particle size distribution (mean diameter and poly-dispersity index) of the nanoparticles, prior to and after drug loading was determined by photon correlation spectroscopy using quasi-elastic light scattering equipment (ZETAPLUS™ particle size analyzer, Brookhaven Instrument Corp., Holtsville, N.Y.) and ZETAPLUS™ particle size software (Version 2.07). To measure particle size, a dilute dispersion of nanoparticles in HEPES buffer (0.1 mg/mL, 0.001 M pH 7.0) was prepared. The same sample was used to measure zeta potential of particles using ZETAPLUS™. Particle size of nanoparticles was also determined by transmission electron microscopy (TEM). A drop of rapamycin-loaded nanoparticles in water was placed on a FORMVAR®-coated copper grid, followed by a negative staining with 2% (w/v) uranyl acetate solution. Particles were visualized using a Philips 201 TEM microscope (Philips/FEI Inc., Briarcliff Manor, N.Y.).

The $^1$H NMR spectra of the copolymer demonstrated the absence of vinyl end group protons of the monomers, indicating that polymerization was complete. The mean hydrodynamic diameter of nanoparticles was ~70 nm with a narrow size distribution (polydispersity index=0.11) and zeta potential (surface charge) of –8.45 mV at pH 7. The particle size of micellar nanosystem increased slightly (mean diameter ~70 vs. ~76 nm) following drug loading. The nanoparticles formed a colloidal dispersion in phosphate buffered saline (PBS). TEM of the nanoparticles demonstrated almost spherical shape, with a mean diameter of 61±7 nm (mean±SD; n=20). The particle size obtained with TEM is smaller than that measured with laser light scattering because the latter measures hydrodynamic diameter that includes hydration of the PEG at the outer layer of the nanoparticle. The drug loading was 4.2% w/w (i.e., 100 mg of formulation contained 4.2 mg of rapamycin); with an encapsulation efficiency of 84% (i.e., 84% of the added drug was trapped in nanoparticles).

Example 2

Drug Release from Nanoparticles

Release of rapamycin from nanoparticles in vitro was determined in PBS (154 mM, pH 7.4) containing 0.1% w/v TWEEN®-80 to maintain the sink condition. The donor chamber of each cell was filled with a 2.5 mL dispersion of nanoparticles (2 mg/mL) in buffer and the receiver chamber was filled with the same buffer. A MILLIPORE® membrane with 0.1 µm pore size (Millipore Co., Bedford, Mass.) was placed between the two chambers. The cells were placed on a shaker maintained at 37° C. and rotated at 100 rpm (ENVIRON®, Lab Line, Melrose Park, Ill.). At predetermined time intervals, the solution from the receiver side was completely removed and replaced with fresh buffer. Rapamycin concentration in the collected samples was determined by HPLC (Shimadzu Scientific Instrument, Inc., Columbia, Md.). The mobile phase consisting of methanol: water (9:1 v/v) delivered at a flow rate of 0.4 mL/minute (pump Model LC-10AT). A 20 µL of sample was injected by an autoinjector (Model SIL-10A) and the separations were achieved using a NOVA-PARK® C-8 column (2×150 mm$^2$, 4 µm size packing; Phenomenex, Torrance, Calif.). Rapamycin levels in the samples were quantified by UV detection ($\lambda$=276 nm, Model SPD-10A VP, Shimadzu). A standard plot of rapamycin (0-50 µg/mL) was prepared under identical conditions.

The release profile of rapamycin from the nanoparticles disclosed herein under in vitro conditions demonstrated a relatively rapid drug release rate during the initial stages (~20% release in 24 hours) with more sustained release thereafter (more than 80% release in 28 days).

Example 3

Anti-Proliferative Effects of Rapamycin-Loaded Nanoparticles

Human vascular smooth muscle cells (Cascade Biologics, Portland, Oreg.) were maintained on medium 231 supplemented with smooth muscle growth supplement (Cascade Biologics) at 37° C. in a humidified, 5% $CO_2$ atmosphere. Cells passaged 3 to 4 times were typically used.

To monitor cell proliferation, cells were seeded at a 5,000 cell per well density in 96-well plates and allowed to attach for 24 hours. Different doses of rapamycin (1 ng/mL to 1,000 ng/mL) either loaded in nanoparticles or in solution (rapamycin dissolved in methanol was diluted in the medium) were used. The concentration of methanol in the medium was kept below 0.1% so that it had no effect on cell proliferation. Cells treated with empty nanoparticles or medium served as respective controls for drug-loaded nanoparticles or drug in solution. The medium in the wells was changed on day two and on every alternate day thereafter with no further addition of drug. Anti-proliferative activity of the drug was monitored for eight days of the study using an MTS assay (CELLTITER 96® AQ$_{ueous}$, Promega, Madison, Wis.). MTS assay reagent (20 µL/well) was added to each well and the plates were incubated for 3 hours at 37° C. in a cell culture incubator. Color intensity was measured at 490 nm using a microplate reader (Bio-Tek Instrument, Winooski, Vt.).

For cell cycle analysis, cells were seeded into T-75 culture flasks at a cell density of 1×10$^6$ cells per flask in 10 mL growth medium and were allowed to attach overnight. The medium from each flask was replaced with a dispersion of rapamycin-loaded nanoparticles in growth medium (dose of rapamycin=50 ng/mL). Two days following treatment, cell monolayers were washed with PBS and the cells were detached by trypsinization. DNA analysis was performed by staining cells with propidium iodide, a fluorescent dye which intercalates between DNA base pairs. The cells were fixed with 70% ethanol, incubated for 1 hour, and 1 mL of Telford reagent was added to the cell suspension. The cellular DNA content was analyzed by a fluorescent activated FACSTARPLUS® flow cytometer operating under Lysis II (Becton Dickinson Immunocytometry Systems, San Jose, Calif.).

Example 4

Balloon Injury and Local Delivery in Rat Carotid Artery

Male Sprag-Dawley rats (240 to 260 grams; Charles River Laboratories, Wilmington, Mass.) were anesthetized with an intraperitoneal injection of a mixture of ketamine (80 mg/kg) and xylazine (10 mg/kg). Through a midline neck incision, the left common, external and internal carotid arteries were exposed by blunt dissection. A 2F Fogarty balloon catheter (Edwards Life Sciences, Irvine, Calif.) was introduced in the left external carotid artery via an arteriotomy and was advanced to the origin of the left common carotid artery. The balloon was inflated sufficiently to generate slight resistance and was withdrawn three times consistently to produce endothelial denudation of the entire length of the left common carotid artery. Upon removal of the balloon catheter, a PE 10 catheter was inserted into the left common carotid artery. The mid and the distal portions of the left common carotid artery and the left internal carotid artery were temporarily tied off. A suspension of rapamycin-loaded nanoparticles (200 µL containing 60 µg of rapamycin equivalent nanoparticles) was infused into the injured carotid artery over 5 minutes at 2 atm of pressure (three, one-minute periods between infusions of 70 µL of the suspension, with a one minute period between infusions). Following infusion of the nanoparticles, the ties were removed and the blood flow was restored. In another group of animals, the same dose of rapamycin-loaded nanoparticles was injected intraperitoneal to demonstrate that the effect of rapamycin on inhibition of restenosis is due to local drug delivery.

Example 5

Arterial Localization of Nanoparticles

To determine localization of nanoparticles in the layers of arterial wall (Intima, Media or Adventitia), particularly with time after infusion, a formulation of nanoparticles containing 6-coumarin dye was infused following balloon injury as described. The physical properties (particle size and zeta potential) of the dye-loaded nanoparticles were similar to the drug-loaded nanoparticles. At one hour and 24 hours following infusion of nanoparticles, the arteries were removed, rinsed, and embedded in O.C.T. compound (Tissue-Tek, Sakura, Torrance, Calif.) and stored in dark at −70° C. until histological evaluation. The frozen blocks were sectioned using a rotary microtome (AO 820, American Optical, Del Mar, Calif.) and viewed with a confocal microscope. The images were captured using a 488-nm filter (Fluorescein), 568-nm filter (Rhodamine), and differential interference contrast using a Zeiss Confocal microscope LSM410 equipped with argon-krypton laser (Carl Zeiss Microimaging, Thornwood, N.Y.).

To determine arterial uptake and drug retention, carotid arteries from both sides were removed at different time points following administration of rapamycin-loaded nanoparticles, arteries were rinsed with saline and blotted dry using an absorbent paper. Each artery was weighed (wet weight), finely cut into small pieces with a scissor, homogenized in 2 mL of distilled water using a tissue homogenizer (Biospace Product Inc, Bartlesville, Okla.) at 1,000 rpm for two minutes, and homogenates were lyophilized for 48 hours. Drug from each dry tissue was extracted by shaking each sample with 1 mL methanol at 37° C. for 48 hours at 150 rpm using an ENVIRON® orbital shaker. The samples were centrifuged at 14,000 rpm for 10 minutes (EPPENDORF® Microcentrifuge, 5417R, Brinkmann Instruments, Westbury, N.Y.) to remove cell debris. The supernatant was analyzed by HPLC for rapamycin content as described herein. A standard plot was prepared using arteries collected from animals which did not receive rapamycin to determine efficiency of drug recovery.

Example 6

Inhibition of Restenosis

After three weeks, rats were anesthetized with an intraperitoneal injection of a mixture of ketamine (80 mg/kg) and xylazine (5 mg/kg). After the intravascular system was cleared, pressure fixation was performed by infusing 10% formaldehyde solution over 5 minutes at 120 mm Hg. Left carotid arteries were retrieved and immersed in the same fixative until sectioned. The arteries were cut into pieces every 3 mm from proximal to distal ends. These pieces of arteries were embedded in paraffin for sectioning, and duplicate slides were stained with hematoxylin-eosin. The medial and intimal areas and luminal area were measured with a computerized digital image analysis system.

For immunohistochemical analysis, samples were incubated with I-VIEW inhibitor to block endogenous peroxidase activity. After washings in PBS, sections were incubated with primary antibody for one hour at room temperature. The following primary antibodies were used: monoclonal mouse 1A4 antibody recognizing α-SM actin (neat, DAKO, Carpenter, Calif.) and monoclonal mouse PC10 antibody for identifying PCNA (1:25 dilution, DAKO, Carpenter, Calif.) and CD31 antibody (1:100 dilution, DAKO, Carpenter, Calif.) for endothelial staining, anti-cleaved caspase-3 (1:200 dilution, Cell Signaling Technology, Beverly, Mass.) apoptotic cells by terminal deoxynucleotidyl transferases (TdT)-mediated dUTP nick end-labeling (TUNEL) method using TUNEL system kit (Promega, Madison, Wis.). Sections were subsequently incubated with I-VIEW biotin and I-VIEW streptavidin-horseradish peroxidase. Sections were visualized using DAB chromogen and were counterstained using I-VIEW copper. The number of cells positive for PCNA and α-SM actin staining was counted at a magnification 400×. Endothelization was calculated as the ratio between the luminal surface covered by CD31 positive cells and the total luminal surfaces.

All the data are presented as mean±SEM. The statistical significance of differences between the untreated and treated groups was determined by a one-way ANOVA. Differences were considered significant if $p<0.005$.

What is claimed is:

1. A sustained-release composition in nanoparticle form consisting essentially of a therapeutic agent and a cross-linked copolymer of an N-alkylacrylamide selected from the group consisting of N-methyl-N-n-propylacrylamide, N-methyl-N-isopropylacrylamide, N-propylmethacrylamide, N-isopropylacrylamide, N—N-diethylacrylamide, N-isopropylmethacrylamide, N-cyclopropylacrylamide, N-ethylmethacrylamide, N-methyl-N-ethylacrylamide, N-cyclopropylmethacrylamide and N-ethylacrylamide, a vinyl monomer selected from the group consisting of a vinyl alcohol, a vinyl ether, a vinyl ester, vinyl pyrrolidone and a combination of said vinyl monomers, and PEGylated maleic acid conjugate, wherein the weight per weight ratio of the N-alkylacrylamide, vinyl monomer and PEGylated maleic acid conjugate is 70-90:9-20:1-10, said therapeutic agent being encapsulated in said copolymer in an amount from 3% to 10% based on said nanoparticle weight, and said composition being effective to release said therapeutic agent for at least 2 to 3 weeks.

2. The sustained-release nanoparticle composition of claim 1, wherein said therapeutic agent is selected from the group consisting of antibiotics, antirestenotics, anti-proliferative agents, anti-neoplastic agents, chemotherapeutic agents, cardiovascular agents, anti-inflammatory agents, immunosuppressive agents, anti-apoptotic and anti-tissue damage agents.

3. The sustained-release nanoparticle composition of claim 1, wherein said therapeutic agent comprises an anti-proliferative agent.

4. The sustained-release nanoparticle composition of claim 1, wherein said ratio is 80:15:5.

5. The sustained-release nanoparticle composition of claim 1, wherein said nanoparticles have an average diameter in the range of 20 nm to 100 nm as measured by transmission electron microscopy.

6. The sustained-release nanoparticle composition of claim 1, wherein said therapeutic agent is an anti-apoptotic agent.

7. The sustained-release nanoparticle composition of claim 6, wherein said anti-apoptotic agent is selected from the group consisting of galectin-3, (-) deprenyl, rapamycin, quercetin and a monoamine oxidase inhibitor.

8. The sustained-release nanoparticle composition of claim 1, wherein said therapeutic agent is rapamycin.

9. A method for localized delivery of a therapeutic agent to a disease site, said method comprising administering to said disease site a therapeutically effective amount of the sustained-release nanoparticle composition as claimed set forth in claim 1.

10. The method of claim 9, wherein said disease site is a site of hyperplasia and said therapeutic agent is an anti-proliferative agent.

11. The method of claim 10, wherein said disease site is a site of restenosis and said anti-proliferative agent is rapamycin.

* * * * *